(12) United States Patent
Nagahama et al.

(10) Patent No.: US 6,984,691 B2
(45) Date of Patent: Jan. 10, 2006

(54) W/O/W COMPOSITE EMULSION

(75) Inventors: Tohru Nagahama, Tokyo (JP); Tomoaki Yoshino, Tokyo (JP)

(73) Assignee: Taisho Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 10/432,933

(22) PCT Filed: Nov. 29, 2001

(86) PCT No.: PCT/JP01/10422

§ 371 (c)(1), (2), (4) Date: May 28, 2003

(87) PCT Pub. No.: WO02/43698

PCT Pub. Date: Jun. 6, 2002

(65) Prior Publication Data

US 2004/0010078 A1    Jan. 15, 2004

(30) Foreign Application Priority Data

Nov. 29, 2000  (JP)  .............................. 2000-362918

(51) Int. Cl.
    C08L 91/00     (2006.01)
    A61K 9/113     (2006.01)
    A61K 47/14     (2006.01)
    A61K 47/30     (2006.01)
    A61K 47/44     (2006.01)

(52) U.S. Cl. ................... 524/801; 524/801; 514/937; 514/938; 514/939; 514/943

(58) Field of Classification Search ............... 524/801; 514/937, 938, 939, 943
See application file for complete search history.

(56) References Cited

U.S. PATENT DOCUMENTS 4,328,149 A  *  5/1982  Morse et al. ............... 524/458
4,931,210 A  *  6/1990  Takahashi et al. ............ 516/54

FOREIGN PATENT DOCUMENTS

| EP | 0 174 377 A1 |   | 3/1986 |
|----|--------------|---|--------|
| JP | 58-143831 A1 |   | 8/1983 |
| JP | 58143831     | * | 8/1983 |
| JP | 59080326     | * | 5/1984 |
| JP | 03-127952 A1 |   | 5/1991 |

(Continued)

OTHER PUBLICATIONS

Translation to Kitaoka et al., JP-59-080326 (1984).*

*Primary Examiner*—Kelechi C. Egwim
(74) *Attorney, Agent, or Firm*—Rader, Fishman & Grauer PLLC

(57) ABSTRACT

A W/O/W type composite emulsion, wherein a W/O type emulsion containing water, an oil ingredient and a lipophilic emulsifier each in a proportion expressed in term of mass ratio falling within a range enclosed with bold lines in FIG. 1 is dispersed in an external aqueous phase with a water-soluble macromolecule blended therein has a sufficient stability, and permits preserving a percent inclusion of medical substances included in an internal aqueous phase of the W/O/W type composite emulsion at a high level.

Because of the characteristics, it is now possible to blend in a liquid formulation medical substances having an unfavorable taste or unstable medical substances which have to date hardly been included in liquid formulations with low viscosity, so that the W/O/W type composite emulsion can be utilized for liquid formulations including a liquid formulation for internal application, injections, etc.

14 Claims, 1 Drawing Sheet

|   | WATER | OILY INGREDIENTS | LIPOPHILIC EMULSIFIER |
|---|-------|------------------|----------------------|
| I | 0.5% | 79.5% | 20% |
| II | 60% | 20% | 20% |
| III | 60% | 2% | 38% |
| IV | 32% | 2% | 66% |
| V | 0.5% | 33.5% | 66% |

FOREIGN PATENT DOCUMENTS

| | | |
|---|---|---|
| JP | 04-099716 A1 | 3/1992 |
| JP | 04-100536 A1 | 4/1992 |
| JP | 10-158152 A1 | 6/1998 |
| JP | 10-203962 A1 | 8/1998 |
| JP | 11-033391 A1 | 2/1999 |
| JP | 11-188256 A1 | 7/1999 |
| JP | 11-240840 A1 | 9/1999 |
| JP | 11240840 * | 9/1999 |
| JP | 2001-151938 A1 | 6/2001 |

* cited by examiner

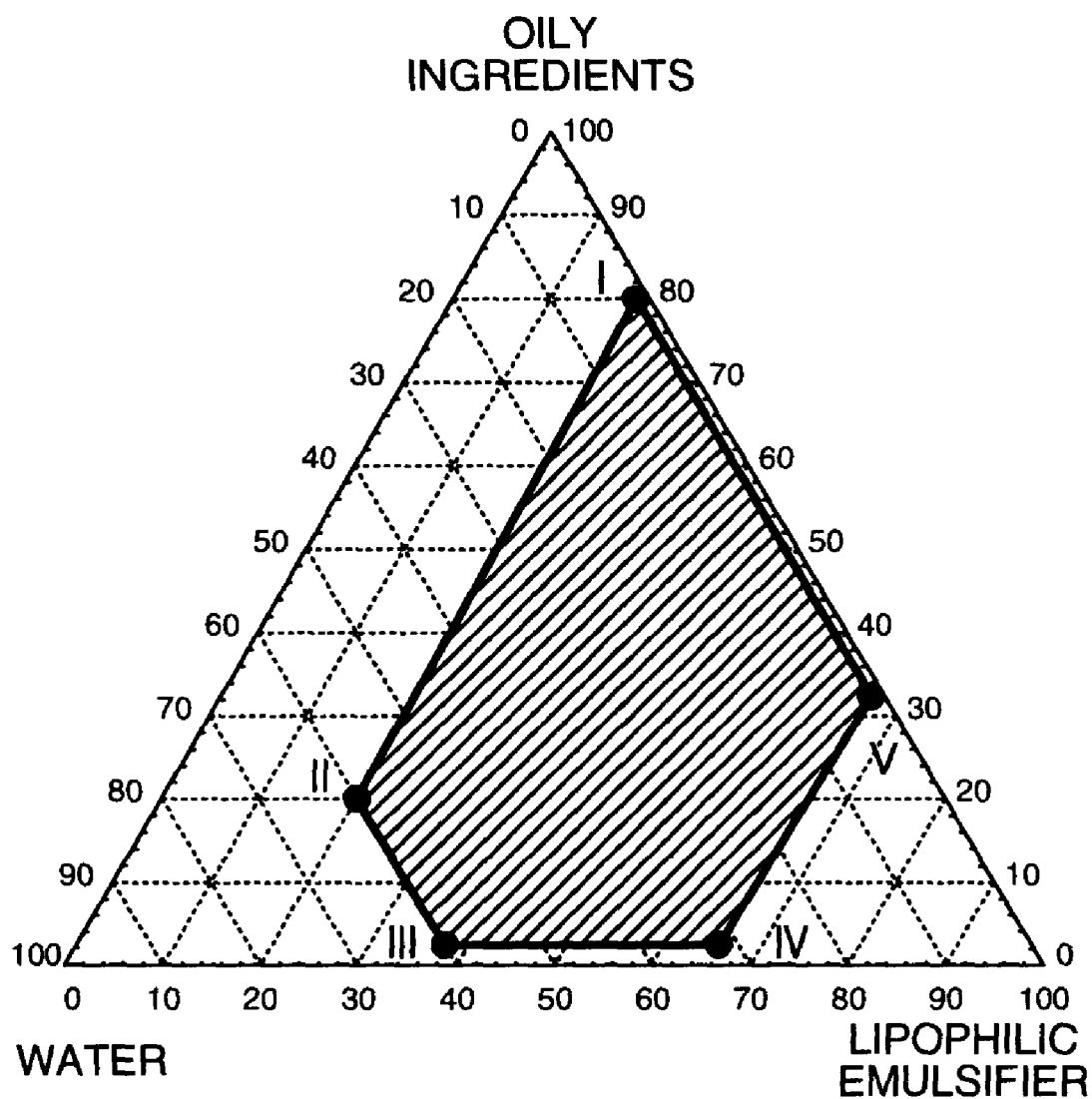

W/O/W COMPOSITE EMULSION

FIELD OF THE INVENTION

The present invention relates to a W/O/W type composite emulsion.

PRIOR ART

Liquid formulations are a type of formulation well adapted to use by ordinary people. For instance, liquid formulations for internal application can easily be administered to the aged people as well as to infants and children, who have low swallowing capability, so that liquid formulations are widely used as a medicine or a functional food.

However, when medical substances having unpleasant taste such as bitterness are blended in a liquid formulation for internal application, the taste of the medical substances is directly felt by the user, so that the taste of the liquid formulation itself becomes disadvantageously unpleasant. Further, in a liquid formulation, the added medical substances easily react with each other, and therefore it has been difficult to blend medical substances each having high reactivity in a liquid formulation.

To prevent the taste of a liquid formulation from becoming unpleasant, the method of masking the unpleasant taste of a liquid formulation by blending various types of taste-improving agents in the liquid formulation is often employed. In this method of masking the unpleasant taste by blending taste-improving agents therein, however, there are several restrictions such as the limited quantity of medical substances which can be blended in the liquid formulation.

As a method of blending medical substances in a liquid formulation in the stable state, the method of emulsifying the liquid formulation is also known. As water-soluble medical substances and fat-soluble medical substances can be blended together in an emulsion, many reports have been made for application of emulsions, for instance, in medicines. However, for conventional O/W type emulsions, it is difficult to prevent the medical substances contained therein from reacting with each other.

W/O/W type composite emulsions are advantageous in that they permit blending of water-soluble medical medicines, which are generally not adapted to blending due to the stability and taste, in an internal aqueous phase. They are also advantageous in that they permit preparation of an administrative preparation in which such medical substances that easily react to each other and can hardly be blended together are incorporated in combination into a preparation, since the medical substances can be isolated from each other by including some of the medical substances in an internal aqueous phase and the others in an external aqueous phase. As the W/O/W type composite emulsions are generally low in their stability, they are used in creamy preparations with high viscosity in which the stability is relatively preserved; however, there has been no report on use of W/O/W composite emulsions in such a preparation that is used as a liquid formulation for internal application with a viscosity of 150 mPa·s or below.

There has generally been known for emulsions that, the smaller the particle diameter of emulsions, the higher the dispersion stability thereof in a liquid formulation is. When the particle diameter of W/O/W type composite emulsion is made smaller, however, medical substances flow out from the internal aqueous phase, which disadvantageously makes the percent inclusion (a relative quantity of medical substances included in the internal aqueous phase) smaller. Therefore, in the range of the particle diameter from 20 to 2000 nm in which the dispersion stability in a liquid formulation can be relatively well preserved, it has been difficult to produce the W/O/W type composite emulsion at a high percent inclusion.

Further the utility value of the W/O/W type composite emulsion becomes higher as the quantity of medical substances which can be included in one particle of the emulsion is larger. However, when the quantity of medical substances included in one particle of emulsion becomes larger, the percent inclusion of medical substances generally becomes lower.

The percent inclusion of medical substances into emulsion can be determined as satisfactory when a value $(B/Log_{10}C)$ obtained by dividing the percent inclusion (%) of medical substances included in the internal aqueous solution of the W/O/W type composite emulsion by a common logarithm of the average particle diameter of the W/O/W type composite emulsion is 27 or more. Unfortunately, there has been no technique allowing for production of emulsions having such low viscosity of 150 mPa·s or below that allows their use as a liquid formulation and at the same time meeting the requirements as described above.

As the conventional technique for production of W/O/W type composite emulsions, JP 4-100536 A discloses, for instance, technique for production of W/O/W type composite emulsions by using polyglycerin-condensated ricinoleic acid ester, a lipophilic emulsifier. However, the resulting emulsion cannot be satisfactorily applied to practical use, because it has an undesirably large particle diameter and undesirably low dispersion stability.

As the technique for obtaining a W/O/W type composite emulsion having a minute particle diameter, JP 4-99716 A describes a technique for producing an injection, but the injection produced by the technique cannot be used as a liquid formulation for internal application because of the unfavorable taste of the emulsifier.

Although W/O/W or S/O/W type emulsions are disclosed, for instance, in JP 3-127952 A, JP 10-158152 A, JP 10-203962 A, JP 11-188256 A, JP 11-240840 A, all the emulsions provided therein have an undesirably large particle diameter.

DISCLOSURE OF THE INVENTION

The inventors of the present invention made an extensive study with an objective to obtain a W/O/W type composite emulsion which has a sufficient stability even in the fine particle state and which can preserve the percent inclusion of medical substances included in the internal aqueous phase thereof at a high level. As a result, they have found that producing a W/O type emulsion by blending water, an oil ingredient and a lipophilic emulsifier each with a specific blend ratio different from that in the products based on the conventional technique and then producing a W/O/W type composite emulsion by dispersing the W/O type emulsion in an aqueous phase thereof with a water-soluble macromolecule provide a W/O/W type composite emulsion which has an extremely small particle diameter and sufficient stability and can preserve the percent inclusion of medical substances included in an internal aqueous phase at a high level. The present invention has been accomplished based on those findings.

Thus, the present invention provides a W/O/W type composite emulsion, wherein a W/O type emulsion comprising water, an oil ingredient and a lipophilic emulsifier each in a proportion expressed in term of mass ratio falling within a range enclosed with bold lines in FIG. 1 is dispersed in an external aqueous phase with a water-soluble macromolecule blended therein.

According to the present invention, there is provided a W/O/W type composite emulsion with an average particle diameter in a range, within which the dispersing stability in a liquid formulation can be preserved easily, of 2000 nm or below, by providing a W/O type emulsion produced as described above while incorporating water, an oil ingredient and a lipophilic emulsifier each in a specific proportion and dispersing the W/O type emulsion in an external aqueous phase with a water-soluble macromolecule, which W/O/W type composite emulsion can preserve the percent inclusion of the medical substances included in the internal aqueous phase at a high level. In addition, the W/O/W type composite emulsion according to the present invention can make the volume of an internal aqueous phase larger, which enables in turn to drastically increase the quantity of medical substances included in each particle of the W/O/W type composite emulsion.

As the lipophilic emulsifier used in the present invention, polyglycerin fatty acid ester having an HLB value of 10 or less is preferable.

In the case described above where polyglycerin fatty acid ester is used as the lipophilic emulsifier, the polymerization degree of the polyglycerin potion is preferably within the range of from 4 to 12. Preferably, the fatty acid portion of the polyglycerin fatty acid ester is an unsaturated fatty acid, more preferably, unsaturated fatty acid having 16 to 22 carbon atoms, and still more preferably, a hydroxy-unsaturated fatty acid. Specifically, oleic acid, linoleic acid, linolenic acid, ricinoleic acid and erucic acid are preferable and ricinoleic acid is particularly preferable.

Those especially preferable polyglycerin-condensed ricinoleic acid esters include tetraglycerin-condensed ricinoleic acid ester, hexaglycerin-condensed ricinoleic acid ester, pentaglycerin-condensed ricinoleic acid ester, decaglycerin-condensed ricinoleic acid ester and the like as well as the mixtures thereof.

Oil ingredients used in the present invention include commonly-used ones such as liquid paraffin, squalane, squalene, tocopherol, tocopherol acetate, tocopherol nicotinate, avocado oil, camellia oil, turtle oil, macadamia nuts oil, corn oil, mink oil, olive oil, rapeseed oil, yolk oil, sesame oil, wheat germ oil, Camellia sasanqua oil, castor oil, safflower oil, cottonseed oil, soybean oil, peanut oil and tricaprilyn, and of these tocopherol acetate is preferable. In addition, fat-soluble medical substances may be blended in the oil ingredients.

The preferable water-soluble macromolecules used in the present invention include water-soluble proteins, water-soluble synthetic polymers, water-soluble polysaccharides and the derivatives thereof.

The water-soluble proteins include casein, sodium caseinate, β-lactoglobulin, α-lactalbumin, albumin, gelatin, soybean protein, and of these casein, sodium caseinate, β-lactoglobulin and α-lactalbumin are preferable.

The water-soluble synthetic polymers include polyvinyl alcohol, polyvinyl pyrrolidone, carboxyvinyl polymer, polyvinyl methyl ether and poly(sodium acrylate), and of these polyvinyl alcohol and polyvinyl pyrrolidone are preferable.

The water-soluble polysaccharides or the derivatives thereof include xanthan gum, gelan gum, dextran, pullulan, gum arabic, carrageenan, locust bean gum, dextrin, guar gum, pectin, sodium alginate, hydroxypropylcellulose, hydroxypropyl methylcellulose, methylcellulose, hydroxyethylcellulose and carboxylmethylcellulose, and of these xanthan gum and hydroxypropylcellulose are preferable.

The water-soluble macromolecules can be used in combination of two or more.

The blend proportion of the water-soluble macromolecule according to the present invention preferably ranges from 0.001 to 20% by mass, and more preferably from 0.01 to 10% by mass, of the external aqueous phase.

When the blend proportion of the water-soluble macromolecule is too small, it is difficult to produce a homogeneous and fine W/O/W type composite emulsion, while the blend proportion of the water-soluble macromolecule is too large, the resultant W/O/W type composite emulsion has an undesirably high viscosity for internal application.

When medical substances having unpleasant taste or easily reacting with other components are blended in the internal aqueous phase of the W/O/W type composite emulsion according to the present invention, the advantage of the present invention is fully exhibited, but even when commonly-used water-soluble medical substances are blended therein, the advantage can be expected in improvement of the stability.

The blend proportion of the water-soluble macromoleculemedical substances that can be blended in the internal aqueous phase varies depending upon the solubility, but the advantages of the present invention can be achieved by adjusting the blend proportions of the oil ingredient and lipophilic emulsifier taking into considerations the quantity of internal aqueous phase after the medical substances have been dissolved therein so as to meet the presently recited blend proportion of each of the components.

In the present invention, commercial value of the product can be improved by optionally blending pharmaceutical agents, other components, taste or odor reforming agents, pH adjusting agents, preservatives and the like in the external aqueous phase so far as the effect of the present invention is not adversely affected.

The W/O/W type composite emulsion according to the present invention can be produced as described below. At first, an oil phase such as an oil ingredient and lipophilic emulsifier is put into a container. The container is set on an agitator such as a vacuum emulsifying machine. Then the mixture is heated while agitating to a temperature in the approximate range of from 50 to 90° C., dissolved and homogenized. Then to the resultant mixture is added gradually a specified quantity of an aqueous phase containing substances and optional additives to be included in the internal aqueous phase, and the resultant mixture is emulsified while agitating the same at a constant temperature in the approximate range of from 50 to 90° C. Thereafter, the resultant emulsion is cooled to 20 to 40° C. while agitating for a certain period of time to obtain a W/O type emulsion. At this point of time, it is preferable that the W/O type emulsion is formed so as to have an average particle diameter of from approximately 10 to 500 nm. The W/O/W type composite emulsion can be produced by further dispersing this W/O type emulsion in an external aqueous phase containing a specified quantity of a water-soluble macromolecule and optional additives with any of the ordinary methods such as high-pressure homogenizer method, high-speed agitating method, ultrasonic wave emulsifying method and membrane emulsifying method. In addition, heating may be performed, if necessary, in the step of preparing the W/O/W type composite emulsion.

BEST MODE FOR CARRYING OUT THE INVENTION

The present invention is further described in detail with reference to Examples and Test Examples.

Example 1

Preparation of W/O Type Emulsion

| a: | Internal aqueous phase | |
| --- | --- | --- |
| | Ferric ammonium citrate | 8.5 g |
| | Water | 76.5 g |
| b: | Oil ingredient | |
| | Tocopherol acetate | 37.5 g |
| c: | Lipophilic emulsifier | |
| | Polyglycerin-condensed ricinoleic acid ester (produced by Sakamoto Yakuhin Kogyo Co., Ltd., CRS-75) | 127.5 g |

Components b and c were heated to 70 to 80° C., and were homogeneously mixed and dissolved. Then the component a was gradually added to the resultant mixture while agitating. The mixture was agitated and emulsified while maintaining the liquid temperature at approximately 70 to 80° C. The resultant emulsion was further agitated for a certain period of time while gradually cooling it to a temperature of from 20 to 40° C. to obtain a W/O type emulsion.

The average particle diameter of the W/O type emulsion determined with a grain size distribution measuring device based on dynamic light scattering system (NICOMP Model 370 (produced by HIAC/ROYCO)) was 113.8 nm.

Preparation of W/O/W Type Composite Emulsion 20 g of the W/O type emulsion obtained as described above was added, while agitating it with a homogenizer, to 180 g of an aqueous solution containing 0.5% by mass of sodium caseinate and 20% by mass of sugar, to obtain a W/O/W type composite emulsion with a relatively large particle diameter. Thereafter, the W/O/W type composite emulsion was passed through a perforated membrane to obtain a fine W/O/W type composite emulsion with an average particle diameter of 799.6 nm. The average particle diameter of the W/O/W type composite emulsion was determined with a grain size distribution measuring device based on laser beam diffraction/scattering system (HORIBA LA-920).

Measurement of Percent Inclusion of Medical Substances

The percent inclusion of the substances included in the W/O/W type composite emulsion was calculated through the following equation:

Percent inclusion (%)=(Wi−Wo×A)/Wi×100 wherein Wi is a mass of substances included in the W/O/W type composite emulsion; Wo is a mass of substances included in the external aqueous phase; and A is a quotient of the mass of external aqueous phase by the mass of W/O/W type composite emulsion ((mass of external aqueous phase)/(mass of W/O/W type composite emulsion)).

The mass of the substances included in the W/O/W type composite emulsion was measured after preprocessing by means of wet cineration method, etc., whereas the mass of the substances included in the external aqueous phase was measured after subjecting the W/O/W type composite emulsion to centrifugation to separate the particles of the W/O/W type composite emulsion from the external aqueous phase, each with atomic absorption method, respectively. As a result, it was found that the percent inclusion of the included substances (the included substance was iron in this case) was 98.29%.

Examples 2 to 8

Preparation of W/O Type Emulsion

Each of the samples was prepared with the composition shown in Table 1 in the same production method as that employed in Example 1. The average particle diameter of the W/O type emulsion was also measured in the same manner as that employed in Example 1.

In the table showing the results in the Examples, FAC indicates ferric ammonium citrate, and PGCR indicates polyglycerin-condensed ricinoleic acid ester (produced by Sakamoto Kogyo Co., Ltd., CRS-75).

Preparation of W/O/W Type Composite Emulsion

The W/O/W type composite emulsion was prepared by the same production method as that employed in Example 1. The average particle diameter of the W/O/W type composite emulsion was also measured in the same manner as that in Example 1.

Measurement of the Percent Inclusion of Included Substances

The percent inclusion of the substances (In this case, the included substance was iron) in the W/O/W type composite emulsion was measured in the same manner as that in Example 1.

TABLE 1

| | | Example 1 | Example 2 | Example 3 | Example 4 | Example 5 | Example 6 | Example 7 | Example 8 |
| --- | --- | --- | --- | --- | --- | --- | --- | --- | --- |
| Composition of W/O type emulsion | Purified water | 76.50 | 76.50 | 76.50 | 76.50 | 76.50 | 76.50 | 76.50 | 76.50 |
| | FAC (g) | 8.50 | 8.50 | 8.50 | 8.50 | 8.50 | 8.50 | 8.50 | 8.50 |
| | PGCR (g) | 127.50 | 127.50 | 127.50 | 127.50 | 127.50 | 127.50 | 127.50 | 127.50 |
| | Tocopherol acetate (g) | 37.50 | 37.50 | 37.50 | 37.50 | 37.50 | 37.50 | 37.50 | 37.50 |
| Average particle diameter of W/O type emulsion (nm) | | 113.8 | 113.8 | 113.8 | 113.8 | 113.8 | 113.8 | 113.8 | 113.8 |
| Composition of | W/O emulsion (nm) | 20 | 5 | 5 | 5 | 5 | 5 | 5 | 5 |

TABLE 1-continued

| | | Example 1 | Example 2 | Example 3 | Example 4 | Example 5 | Example 6 | Example 7 | Example 8 |
|---|---|---|---|---|---|---|---|---|---|
| W/O/W type composite emulsion | Sodium caseinate (g) | 0.9 | — | — | — | — | — | — | — |
| | Polyvinyl alcohol (g) | — | 0.225 | 0.9 | 2.25 | — | — | — | 0.95 |
| | Polyvinyl pyrrolidone (g) | — | — | — | — | 0.45 | — | — | — |
| | Hydroxypropyl-cellulose (g) | — | — | — | — | — | 0.225 | — | — |
| | Xanthan gum (g) | — | — | — | — | — | — | 0.0225 | — |
| | Sugar (g) | 36 | 9 | 9 | 9 | 9 | 9 | 9 | 19 |
| | Purified water (g) | 143.1 | 35.775 | 35.1 | 33.75 | 35.5 | 35.775 | 35.9775 | 75.05 |
| Average particle diameter of W/O/W type composite emulsion (nm): C | | 799.6 | 614.1 | 569.8 | 560.7 | 737.9 | 592.6 | 772.5 | 233.6 |
| Percent inclusion of iron (%): B | | 98.29 | 99.01 | 99.03 | 98.83 | 100.0 | 99.13 | 99.89 | 97.92 |
| B/Log$_{10}$C | | 33.86 | 35.51 | 35.94 | 35.95 | 34.87 | 35.75 | 34.59 | 41.34 |

As clearly shown in Table 1, when the W/O type emulsions having the blend proportions within the range according to the present invention are dispersed in an external aqueous phase with a water-soluble macromolecule such as water-soluble protein, water-soluble synthetic polymer or water-soluble polysaccharide, very fine W/O/W type composite emulsions with a high percent inclusion of medical substances could be obtained. Further, the W/O/W type composite emulsions were very fine as well as they met the requirement that the value obtained by dividing the percent inclusion (%) of the medical substances dissolved in the internal aqueous phase of the W/O/W type composite emulsion by the common logarithm for the average particle diameter of the W/O/W type composite emulsion (nm) (B/Log$_{10}$ C in Table 1) is 27 or more (See Examples 1 to 8).

Examples 9 to 15 and Comparative Examples 1 to 5

Preparation of W/O Type Emulsion

Each of the samples was prepared with the composition shown in Table 2 or 3 by the same production method as that employed in Example 1. The average particle diameter of the W/O type emulsion was also measured in the same manner as that employed in Example 1.

Preparation of W/O/W Type Composite Emulsion 10 g of the W/O type emulsion obtained as described above was added, while agitating with a magnetic stirrer or a homogenizer, to 90 g of an aqueous solution containing 2% by mass of polyvinyl alcohol and 20% by mass of sugar to obtain a first W/O/W type composite emulsion with a relatively large particle diameter. The first W/O/W type composite emulsion was passed through a perforated membrane to obtain a fine W/O/W type composite emulsion. The average particle diameter of the fine W/O/W type composite emulsion was measured with a grain size distribution measurement device based on the laser diffraction/scattering system (HORIBA LA-920).

Measurement of the Percent Inclusion of Medical Substances

The percent inclusion of the included substances (the included substance was iron in the Examples herein) in the fine W/O/W type composite emulsion was measured in the same manner as that employed in Example 1.

TABLE 2

| | | Example 9 | Example 10 | Example 11 | Example 12 | Example 13 | Example 14 | Example 15 |
|---|---|---|---|---|---|---|---|---|
| Composition of W/O type emulsion | Purified water | 45.00 | 58.50 | 76.50 | 90.00 | 90.00 | 76.50 | 76.50 |
| | FAC (g) | 5.00 | 6.50 | 8.50 | 10.00 | 10.00 | 8.50 | 8.50 |
| | PGCR (g) | 75.00 | 97.50 | 127.50 | 100.00 | 75.00 | 102.50 | 77.50 |
| | Tocopherol acetate (g) | 125.00 | 87.50 | 37.50 | 50.00 | 75.00 | 62.50 | 87.50 |
| Average particle diameter of W/O type emulsion (nm) | | 203.3 | 162.1 | 113.8 | 147.6 | 182.4 | 140.0 | 204.0 |
| Composition of W/O/W type composite emulsion | W/O emulsion (nm) | 10 | 10 | 10 | 10 | 10 | 10 | 10 |
| | Polyvinyl alcohol (g) | 1.8 | 1.8 | 1.8 | 1.8 | 1.8 | 1.8 | 1.8 |
| | Sugar (g) | 18 | 18 | 18 | 18 | 18 | 18 | 18 |
| | Purified water (g) | 70.2 | 70.2 | 70.2 | 70.2 | 70.2 | 70.2 | 70.2 |
| Average particle diameter of W/O/W type composite emulsion (nm): C | | 420.5 | 452.2 | 556.0 | 563.3 | 489.6 | 494.7 | 456.4 |

TABLE 2-continued

|  | Example 9 | Example 10 | Example 11 | Example 12 | Example 13 | Example 14 | Example 15 |
|---|---|---|---|---|---|---|---|
| Percent inclusion of iron (%): B | 91.94 | 99.67 | 99.65 | 99.32 | 92.65 | 99.50 | 89.19 |
| $B/Log_{10}C$ | 35.04 | 37.54 | 36.30 | 36.11 | 34.44 | 36.93 | 33.54 |

TABLE 3

| | | Comparative Example 1 | Comparative Example 2 | Comparative Example 3 | Comparative Example 4 | Comparative Example 5 |
|---|---|---|---|---|---|---|
| Composition of W/O type emulsion | Purified water | 27.00 | 75.00 | 70.62 | 64.42 | 45.00 |
| | FAC (g) | 3.00 | 8.33 | 7.85 | 7.16 | 5.00 |
| | PGCR (g) | 45.00 | 41.67 | 6.54 | 13.42 | 50.00 |
| | Tocopherol acetate (g) | 175.00 | 125.00 | 15.00 | 15.00 | 0.00 |
| Average particle diameter of W/O type emulsion (nm) | | 190.5 | 189.8 | Not produced | Not produced | Not produced |
| Composition of W/O/W type composite emulsion | W/O emulsion (nm) | 10 | 10 | — | — | — |
| | Polyvinyl alcohol (g) | 1.8 | 1.8 | — | — | — |
| | Sugar (g) | 18 | 18 | — | — | — |
| | Purified water (g) | 70.2 | 70.2 | — | — | — |
| Average particle diameter of W/O/W type composite emulsion (nm): C | | 364.7 | 425.5 | — | — | — |
| Percent inclusion of iron (%): B | | 57.34 | 61.24 | — | — | — |
| $B/Log_{10}C$ | | 22.38 | 23.29 | — | — | — |

As described above, when the W/O type emulsion having blend proportions within the range according to the present invention is dispersed in an external aqueous phase with a water-soluble macromolecule, a very fine W/O/W type composite emulsions with a high percent inclusion of medical substances could be obtained. Further, the W/O/W type composite emulsions were very fine as well as they met the requirement that the value obtained by dividing the percent inclusion (%) of the medical substances dissolved in the internal aqueous phase of the W/O/W type composite emulsion by the common logarithm for the average particle diameter of the W/O/W type composite emulsion (nm) ($B/Log_{10}C$ in Table 1) is 27 or more (See Examples 9 to 15). To the contrary, when the composition of the W/O type emulsion was outside the range according to the present invention, any W/O/W type composite emulsion with excellent characteristics could not be obtained (See Comparative examples 1 to 5).

INDUSTRIAL APPLICABILITY

With the present invention, it has become possible to blend medical substances each with unfavorable taste or unstable medical substances even in a liquid solution of low viscosity.

Because of the characteristics, now even the medical substances, which have hardly been blended in a liquid formulation for internal application, an injection or the like, can be used for production of medical drugs.

BRIEF DESCRIPTION OF THE DRAWINGS

FIG. 1 is a view showing the range of composition, in which the advantages of the invention can be obtained, plotted with the blend proportion of the lipophilic emulsifier along the bottom edge, that of the water along the left sloped edge, and that of the oil ingredient along the right sloped edges, respectively.

What is claimed is:

1. A W/O/W type composite emulsion,
   wherein a W/O type emulsion comprising water, an oil ingredient and a lipophilic emulsifier each in a proportion expressed in term of mass ratio falling within a range enclosed with bold lines in FIG. 1 is dispersed in an external aqueous phase with a water-soluble macromolecule blended therein,
   wherein the external aqueous phase with the water-soluble macromolecule blended therein comprises from 0.001 to 20% by mass of the water-soluble macromolecule, and
   wherein the lipophilic emulsifier is a polyglycerin unsaturated fatty acid ester having an HLB value of 10 or below.

2. The W/O/W type composite emulsion according to claim 1, wherein the emulsion has an average particle diameter falling within the range of from 20 to 2000 nm.

3. The W/O/W type composite emulsion according to claim 1, wherein the polyglycerin unsaturated fatty acid ester is a polyglycerin-condensated ricinoleic acid ester.

4. The W/O/W type composite emulsion according to claim 1, wherein the water-soluble macromolecule is one or more members selected from the group consisting of water-soluble proteins, water-soluble synthetic polymers, water-soluble polysaccharides and derivatives thereof.

5. The W/O/W type composite emulsion according to claim 1, wherein the water-soluble macromolecule is a water-soluble protein.

6. The W/O/W type composite emulsion according to claim 5, wherein the water-soluble protein is casein, sodium caseinate, β-lactoglobulin or α-lactoalubumin.

7. The W/O/W type composite emulsion according to claim 1, wherein the water-soluble macromolecule is a water-soluble synthetic polymer.

8. The W/O/W type composite emulsion according to claim 7, wherein the water-soluble synthetic polymer is polyvinyl alcohol or polyvinyl pyrrolidone.

9. The W/O/W type composite emulsion according to claim 1, wherein the water-soluble macromolecule is polysaccharide or a derivative thereof.

10. The W/O/W type composite emulsion according to claim 9, wherein the water-soluble polysaccharide or a derivative thereof is xanthan gum or hydroxy propylcellulose.

11. The W/O/W type composite emulsion according to claim 1, wherein the emulsion has a value obtained by dividing a percent inclusion (%) of a medical substances dissolved in an internal aqueous phase of the W/O/W type composite emulsion by a common logarithm for an average particle diameter (nm) of the W/O/W type composite emulsion of 27 or more.

12. The W/O/W type composite emulsion according to claim 1, wherein the emulsion has a viscosity of 150 mPa·s or below.

13. The W/O/W type composite emulsion according to claim 1, wherein the emulsion is a liquid formulation for internal application.

14. The W/O/W type composite emulsion according to claim 7, wherein the water-soluble synthetic polymer is polyvinyl alcohol.

* * * * *